United States Patent [19]

LaFontaine

[11] Patent Number: 5,676,693
[45] Date of Patent: Oct. 14, 1997

[54] ELECTROPHYSIOLOGY DEVICE

[75] Inventor: Daniel Marc LaFontaine, Plymouth, Minn.

[73] Assignee: Scimed Life Systems, Inc., Maple Grove, Minn.

[21] Appl. No.: 259,663

[22] Filed: Jun. 14, 1994

Related U.S. Application Data

[63] Continuation-in-part of Ser. No. 976,406, Nov. 13, 1992, abandoned.

[51] Int. Cl.$^6$ .................................................... A61N 1/00
[52] U.S. Cl. ..................................................... 607/116
[58] Field of Search .................................... 128/639, 642; 607/115–116, 120, 122, 124, 133–8, 154; 606/32, 41, 48, 194; 604/52–3, 96, 104

[56] References Cited

U.S. PATENT DOCUMENTS

| Re. 33,925 | 5/1992 | Bales et al. |
| 623,022 | 4/1899 | Johnson ............................ 607/133 |
| 2,043,083 | 6/1936 | Wappler . |
| 3,545,428 | 12/1970 | Webster, Jr. . |
| 4,169,464 | 10/1979 | Obrez . |
| 4,573,473 | 3/1986 | Hess . |
| 4,576,177 | 3/1986 | Webster, Jr. . |
| 4,628,937 | 12/1986 | Hess et al. . |
| 4,641,649 | 2/1987 | Walinsky et al. . |
| 4,660,571 | 4/1987 | Hess et al. . |
| 4,682,596 | 7/1987 | Bales et al. . |
| 4,699,147 | 10/1987 | Chilson et al. . |
| 4,777,955 | 10/1988 | Brayton et al. . |
| 4,785,815 | 11/1988 | Cohen . |
| 4,832,048 | 5/1989 | Cohen . |
| 4,896,671 | 1/1990 | Cunningham et al. . |
| 4,945,912 | 8/1990 | Langberg . |
| 4,966,597 | 10/1990 | Cosman . |
| 4,997,431 | 3/1991 | Isner et al. . |
| 5,083,565 | 1/1992 | Parins . |
| 5,122,137 | 6/1992 | Lennox . |
| 5,151,100 | 9/1992 | Abele et al. . |
| 5,154,501 | 10/1992 | Svenson et al. . |
| 5,156,151 | 10/1992 | Imran . |
| 5,172,699 | 12/1992 | Svenson et al. . |
| 5,215,103 | 6/1993 | Desai . |
| 5,222,501 | 6/1993 | Ideker et al. . |
| 5,228,442 | 7/1993 | Imran . |
| 5,230,349 | 7/1993 | Langberg . |
| 5,236,424 | 8/1993 | Imran . |
| 5,237,996 | 8/1993 | Waldman et al. . |
| 5,239,999 | 8/1993 | Imran . |
| 5,255,678 | 10/1993 | Deslauriers et al. . |
| 5,255,679 | 10/1993 | Imran . |
| 5,263,493 | 11/1993 | Avitall . |
| 5,275,162 | 1/1994 | Edwards et al. . |
| 5,279,299 | 1/1994 | Imran . |
| 5,281,212 | 1/1994 | Savage et al. . |
| 5,281,213 | 1/1994 | Milder et al. . |
| 5,281,215 | 1/1994 | Milder . |
| 5,281,217 | 1/1994 | Edwards et al. . |
| 5,281,218 | 1/1994 | Imran . |
| 5,293,868 | 3/1994 | Nardella . |
| 5,295,484 | 3/1994 | Marcus et al. . |

(List continued on next page.)

OTHER PUBLICATIONS

Ruffy et al., "Radiofrequency Delivery Through an Endocardial Cooled Catheter Results in Increased Lesion Size", Abstract No. 0872.

Bergau et al., "Porous Metal Tipped Catheter Produces Larger Radiofrequency Lesions Through Tip Cooling", Abstract No. 0873.

Sykes et al., "Cooled Tip Ablation Results in Increased Radiofrequency Power Delivery and Lesion Size", Abstract No. 167.

*Primary Examiner*—Angela D. Sykes
*Attorney, Agent, or Firm*—Merchant, Gould, Smith, Edell, Welter & Schmidt, P.A.

[57] ABSTRACT

An ablation and mapping catheter is disclosed which incorporates a fluid electrode for contacting tissue. The fluid emerges along the length of the catheter to generate a linear lesion in the cardiac tissue.

2 Claims, 2 Drawing Sheets

U.S. PATENT DOCUMENTS

| | | |
|---|---|---|
| 5,309,910 | 5/1994 | Edwards et al. . |
| 5,313,943 | 5/1994 | Houser et al. . |
| 5,314,466 | 5/1994 | Stern et al. . |
| 5,324,284 | 6/1994 | Imran . |
| 5,327,889 | 7/1994 | Imran . |
| 5,330,466 | 7/1994 | Imran . |
| 5,334,145 | 8/1994 | Lundquist et al. . |

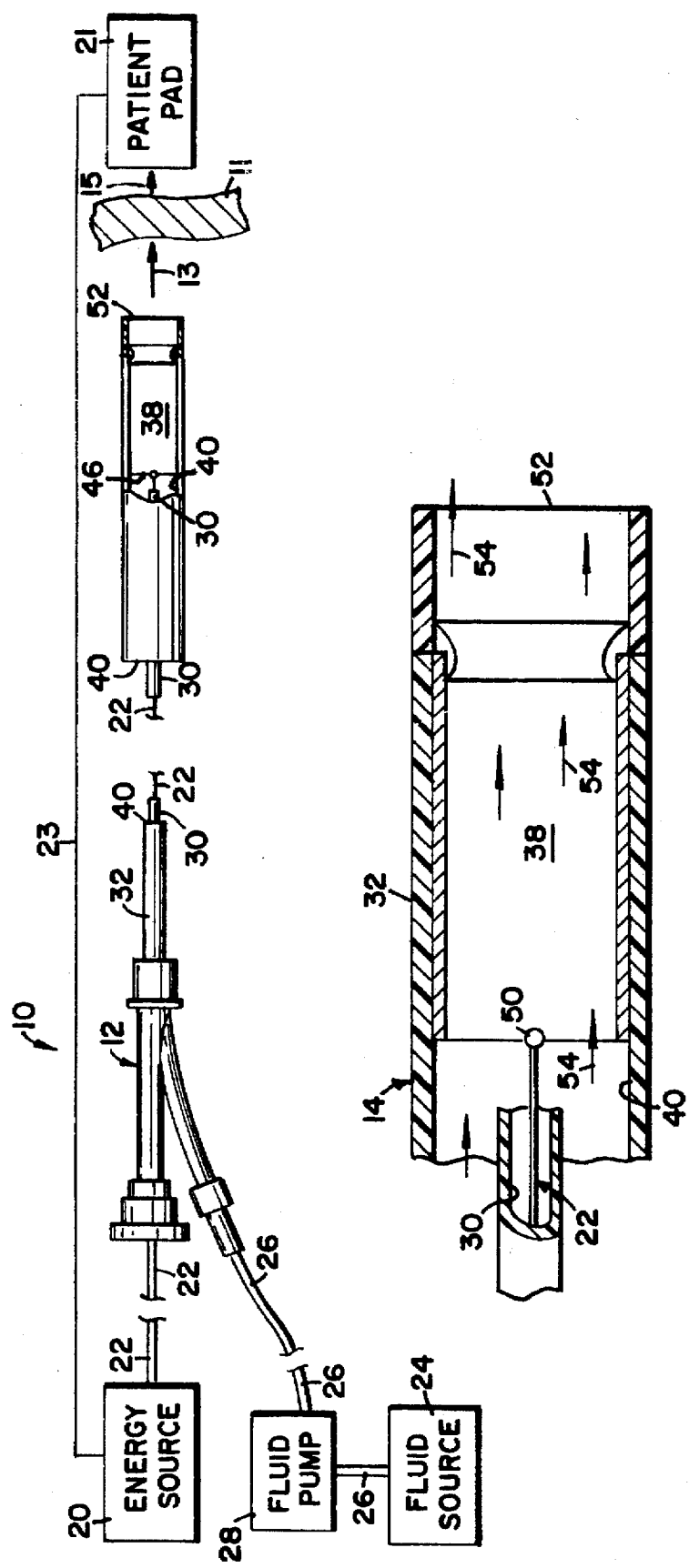

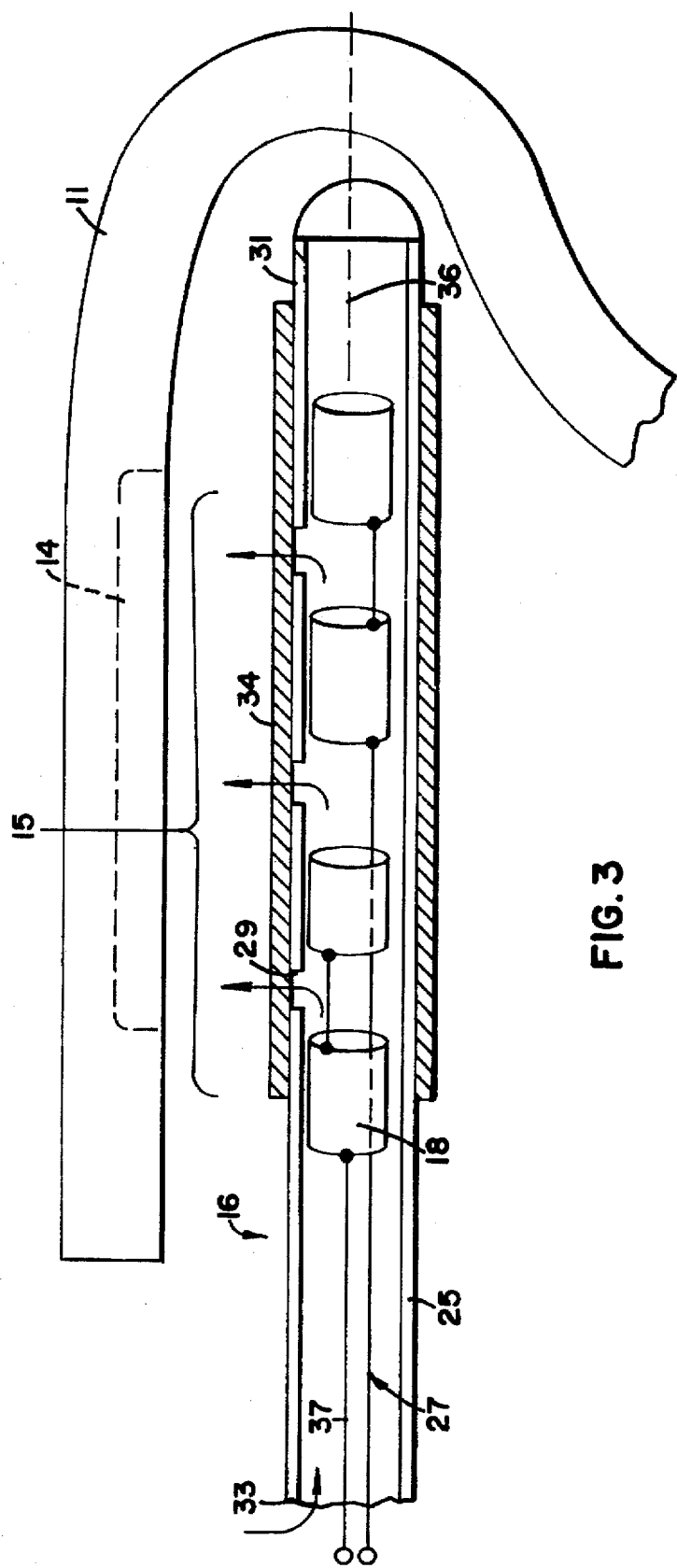

ELECTROPHYSIOLOGY DEVICE

CROSS REFERENCE TO RELATED APPLICATIONS

The present application is a continuation-in-part of U.S. patent application entitled "Electrophysiology Energy Treatment Devices and Methods of Use", filed Nov. 13, 1992, and having Ser. No. 07/976,406, now abandoned. This parent application is incorporated by reference in its entirety.

FIELD OF THE INVENTION

The present invention relates to electrophysiology and more particularly to an ablation of device of and method of operation.

BACKGROUND ART

Arrhythmias can be treated in a number of ways. The traditional treatment has been the systemic administration of anti-arrythmia drugs. However there is a narrow difference between a therapeutic dose and a toxic dose of the most effective drugs. In many instances the drugs induce bradycardia and the patient may receive a heart pacemaker to treat this induced condition.

Another approach is to treat the arrythmia with electrical stimulation of the ventricle to interrupt the arrythmia and convert the heart to normal sinus rhythm. This process maybe performed with an implanted device.

A third approach is ablation. Many arrythmia result from accessory electrical pathways which participate in the generation and continuation of tachy-arrhythmias. It is possible to destroy these accessory pathways by selectively ablating the offending tissue. The application of heat or other energy disrupts and injures the tissue and slows down or prevents the conduction of electrical impulses. The principle benefits of ablation therapies flow from the fact that no implantable device is required nor is a prolonged and expensive drug therapy required. Thus the patient experiences an improved quality of life at a reduced overall cost.

The principal problems related to ablation stem from the requirement to identify the conduction disturbances and then to deliver the ablation energy to the same selected conduction site. This is exceedingly difficult to do given the constant motion of the heart. The energy densities used for radio-frequency ablation are sufficient to "boil" the blood and cause tissue to adhere to the catheter tip. Therefore these therapies must be delivered with care. Therefore there exists a continuing need to improve the ability to delver ablation energy to heart tissue.

SUMMARY

The present invention is a catheter system that can be used for contact mapping and for the delivery of radio-frequency energy along a segment of the catheter which forms a "linear" lesion in the tissue. The catheter relies on a fluid electrode to conduct the RF energy to the tissue. The fluid electrode is preferably a normal saline solution delivered from a pump or the like under the control of the physician. A porus dielectric surface helps to direct the fluid electrode into contact with the tissue.

BRIEF DESCRIPTION OF THE DRAWINGS

The various figures of the drawing set forth an illustrative and exemplary form of the invention. Throughout the various figures identical reference numerals refer to identical structures, wherein:

FIG. 1 is a view of the invention with the distal tip enlarged to clarify certain details of construction;

FIG. 2 is an enlarged view of the distal portion of the of the invention;

FIG. 3 is a view of an alternative embodiment of the invention.

DETAILED DESCRIPTION OF THE INVENTION

FIG. 1 shows the electrophysiology device 10 as part of system. The system includes an energy source 20, a fluid pump 28 coupled to a fluid source 24 through an appropriate tube 26. The fluid pump 24 draws fluid from the fluid source and forces fluid though the central fluid lumen 40 of the catheter 32. A Y-shaped manifold 12 couples the energy source 20 and the fluid system to the catheter 32.

The energy source 20 is coupled to the electrode 38 through a wire 22. This wire 22 passes through a sheath 30 and terminates at a connection 50 located on an electrode 38. The RF energy exits the distal open end 52 of the catheter 32 and passes through the heart tissue 11 as indicated by arrow 13. RF current passing through the heart tissue 11 is collected at the exterior of the patient through a patient pad 21 and is returned to the energy source 20 through return path wire 23 completing the electrical circuit. Experimental work has been performed with an energy source delivering approximately 50 Watts of power delivered into 100 Ohms at about 500 KHz.

The RF energy is confined and directed by a fluid flowing through the fluid lumen 40 of catheter 32 tube. In general, a reservoir or fluid source 24 is provided to store an electrolyte fluid shown in the figure by arrow 54. In practice the electrolyte is a saline solution formed by the addition of 35 G of NaCl to 100 ml of water. This balanced saline works well but higher ionic concentrations may be more effective for some applications where the additional salinity is well tolerated. A modest flow of electrolyte 52 is induced by pump 28 to direct fluid flow against the cardiac tissue 11. In use, the moving saline forms a fluid electrode to assist in the delivery of energy to the tissue 11.

FIG. 2 shows a detail of the distal end of the catheter 32. The drawing shows that the fluid 54 receives the RF energy by passing over the interior of electrode 38. This electrode 38 is located a short distance from the open end 52 of the catheter 32. In general, it is desirable to have a short path length from the electrode 28 to the tissue 11. But it is also desirable to locate the electrode 38 a sufficient distance from the tissue 11 to prevent adhesions and the like from contaminating the surface of the electrode 38. The catheter shown in FIG.2 is particularly effective in making relatively isolated lesions in part because the fluid exits the catheter "axially" at the very distal tip of the catheter 32 body.

FIG. 3 shows a catheter 16 that is adapted to generate a "linear" lesion 14 which extends along the length of the active zone 15 of the catheter 15. In this construction a number of electrodes typified by electrode 18 are aligned along the length of the catheter body 25. The electrodes are coupled to the energy source or other switching structures through wires typified by wire 37. The catheter body 25 has an axis 36. The central lumen 27 of the catheter body 25 is coupled to the fluid source 28 (not shown). The fluid as it moves into the active zone 15 connects to the energy source 20 (not shown) and exits from the catheter body 25 "radially" by migrating through several holes typified by hole or aperture 29. A porous dielectric sheath 34 overlays the hole pattern and helps to regulate the passage of fluid from the lumen 27. The porus sheath 34 places a porus surface proximate the tissue 11. The multiple electrode sites permit the catheter to be quite flexible over the length of the distal segment. If each electrode set is independently accessible through separate connections for mapping studies then the catheter 16 may be used for mapping when the central lumen 27 is filed with a dielectric fluid. Once the ectopic site has been located the central lumen may be quickly filled with the non dielectric, electrolyte saline solution to perform ablation. In general, the presence of saline in the lumen will partially "short" out the electrodes and during ablation the electrode will be connected in parallel to carry the RF currents. It is also possible to use the individual sets of electrodes to "focus" energy along the length of the active zone even in the presence of saline, especially if the salt concentration is low. It should be appreciated that if dielectric tubes were provided to each electrode site then multiple spot ablation could be performed at selected sites. However, it is believed that the ability to generate a linear connected lesion will prove more effective at removing accessory pathways.

What is claimed is:

1. An electrophysiology device for treating tissue by energy delivered from an energy source, comprising:

an elongate catheter body having a lumen for carrying fluid and having a distal end and a proximal end;

a plurality of electrodes located proximate said distal end;

a wire for connection to at least one of said electrodes and to said energy source;

at least one aperture in said catheter body communicating with said lumen;

a porous dielectric sheath located proximate said aperture and located proximate at least one of said electrodes whereby said tissue is insulated from said direct contact with said electrode by said porous dielectric sheath;

a source of electrolyte fluid in communication with said lumen;

whereby, energy from said energy source is directed by said wire from said energy source to said electrode, and energy is coupled to said electrolyte fluid at said electrode and communicated to said tissue through said porous dielectric sheath;

at least some of said electrodes having an independent electrical connection at said proximal end of said elongate catheter body, whereby adjacent sets of electrodes may be individually accessed.

2. A method of treating tissue comprising the steps of:

(a) locating a multiple electrode catheter body proximate said tissue, said catheter body having a proximal end and a distal end and more than one electrode in said distal end; at least some of said electrodes having an independent electrical connection to said proximal end;

(b) positioning a porous dielectric surface between each of said electrodes and said tissue, said porous dielectric surface located adjacent said tissue;

(c) directing electrolyte fluid into contact with said porous dielectric surface, whereby contact with tissue occurs, through said porous dielectric surface;

(d) passing radio frequency current through said tissue by passing radio frequency current through said electrodes and through said electrolyte fluid, and through said porous dielectric surface.

* * * * *